(12) United States Patent
Borst et al.

(10) Patent No.: US 10,808,129 B2
(45) Date of Patent: Oct. 20, 2020

(54) METHINE DYES

(71) Applicant: LANXESS Deutschland GmbH, Cologne (DE)

(72) Inventors: Hans-Ulrich Borst, Elsdorf (DE); Stephan Michaelis, Odenthal (DE); Frank Linke, Cologne (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 16/155,111

(22) Filed: Oct. 9, 2018

(65) Prior Publication Data

US 2019/0112487 A1    Apr. 18, 2019

(30) Foreign Application Priority Data

Oct. 13, 2017  (EP) .................... 17196377

(51) Int. Cl.
| | |
|---|---|
| C07D 403/06 | (2006.01) |
| C09B 23/10 | (2006.01) |
| C08K 5/3462 | (2006.01) |
| C08J 3/12 | (2006.01) |
| C08J 3/20 | (2006.01) |
| D01F 1/06 | (2006.01) |
| C08K 5/00 | (2006.01) |

(52) U.S. Cl.
CPC ............. *C09B 23/105* (2013.01); *C08J 3/12* (2013.01); *C08J 3/20* (2013.01); *C08K 5/3462* (2013.01); *C07D 403/06* (2013.01); *C08J 2333/12* (2013.01); *C08J 2377/00* (2013.01); *C08K 5/0041* (2013.01); *D01F 1/06* (2013.01)

(58) Field of Classification Search
CPC .................................................. C07D 403/06
See application file for complete search history.

(56) References Cited

U.S. PATENT DOCUMENTS

| | | |
|---|---|---|
| 4,622,391 A | 11/1986 | Lorenz et al. |
| 4,628,082 A | 12/1986 | Lorenz et al. |
| 4,757,046 A | 7/1988 | Byers et al. |
| 5,457,188 A | 10/1995 | Zimmermann |
| 6,140,384 A | 10/2000 | Sorori et al. |
| 9,754,084 B2 | 9/2017 | Rolle et al. |
| 2017/0349752 A1 | 12/2017 | Borst et al. |

FOREIGN PATENT DOCUMENTS

JP    2014130250 A2    7/2014

OTHER PUBLICATIONS

RN 115725-78-5 Registry, 1988.*
RN 860449-36-1 Registry, 2005.*
Schwetlick, B.K., Organikum, VEB Deutscher Verlag der Wissenschaften, Berlin, 15th edition 1977, pp. 260, 253, 674.
Kulinich, A.V., et al., "Synthesis, Structure, and Solvatochromism of Merocyanine Dyes Based on Barbituric Acid", Russian Journal of General Chemistry, 2006, vol. 76, No. 9, Pleiades Publishing Inc. pp. 1441-1457.
Wurthner, F, et al., Molecular Design of Thermally Stable Glassforming Merocyanine Dyes:, J. Inf. Recording, 2000, vol. 25, Overseas Publishers Association N.V., pp. 69-86.
European Search Report from corresponding European Application No. 17196377, dated Apr. 19, 2018, three pages.
Bong Rae Cho, et al., Molecular hyperpolarizabilities of barbituric acid and cyclobutene-1,2-dione derivatives, Electronic and steric effects:, J. Chem. Soc., Perkin Trans. 2, 1996, available on the Internet at http://pubs.rsc.org/en/content/article/pdf/1996/p2/p29960002141, pp. 2141-2144.

* cited by examiner

*Primary Examiner* — Brian E McDowell
(74) *Attorney, Agent, or Firm* — Nicanor A. Kohncke

(57) ABSTRACT

The present invention relates to novel methine dyes, methods for the preparation thereof and use thereof for dyeing plastics, especially polyamides, so as to obtain yellow to orange colourings with improved light fastness and improved thermal stability. Methine dyes for example accord to the formula (I)

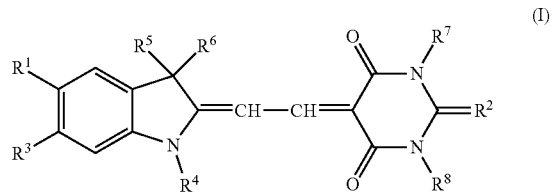

in which
$R^1$ is hydrogen, halogen, alkyl, COOH or COOR$^9$,
$R^2$ is oxygen or sulfur,
$R^3$ is hydrogen, halogen, COOH, COOR$^{10}$ or CN,
$R^4$ is alkyl or phenyl,
$R^5$ and $R^6$ are each independently alkyl,
$R^7$ and $R^8$ are each independently hydrogen, halogen, alkyl or COOR$^{11}$, and
$R^9$, $R^{10}$ and $R^{11}$ are each independently alkyl.

4 Claims, No Drawings

METHINE DYES

The present invention relates to novel methine dyes, methods for the preparation thereof and use thereof for dyeing plastics.

BACKGROUND OF THE INVENTION

Although there are already numerous yellow dyes on the market for colouring plastics, demand still exists for novel dyes with improved properties. In particular, there is a demand for the known dyes to be improved with respect to their fastness. This applies in particular in the case of the use for bulk colouration of polyamide.

The bulk colouration of synthetic polyamides presents higher requirements of the colourants used than the bulk colouration of other plastics. The processing temperatures of synthetic polyamides, particularly in combination with glass fibres, are considerably higher and also the chemical reactivity of molten polyamides, especially of nylon-6.6, is substantially higher such that the heat stability of the colourants used has to be exceptionally good. Pigments generally have high thermal stability. However, there are few pigments which satisfy the high requirements in the case of bulk colouration of plastics, particularly if high light resistance is also additionally required.

Pigments are known from the prior art which are suitable for colouring plastics in shades of yellow.

DE-A 3543512 A1 describes pigments based on azo lakes (Bayplast® yellow G) which may be used for colouring polyamide in shades of yellow.

EP-A 0074515 discloses pigments based on nickel azo-barbituric acid complexes which may likewise be used to achieve yellow colouring of polyamide.

Furthermore, long known is the use of Pigment Yellow 192 (C.I. 507300) to achieve yellow colouration of plastic.

Although the pigments mentioned have good thermal stability, no transparent colouration of plastics can be achieved therewith. Pigments can also impair the mechanical properties of the polymers. The use of solvent dyes is known from the prior art in order to colour plastics in transparent shades of yellow. The mechanical properties of polymers are generally not adversely affected by dyes.

Known solvent yellow dyes are e.g. Solvent Yellow 114 (C.I. 47020) from the class of quinophthalone dyes, Solvent Yellow 160:1 (C.I. 55165) from the class of coumarin dyes and also Solvent Yellow 179 (N-2-((4-cyclohexyl)phenoxy) ethyl-N-ethyl-4-(2,2-dicyanoethenyl)-3-methylaniline) and Solvent Yellow 93 (C.I. 48160), both from the class of methine dyes.

The properties of these yellow colourants known from the prior art are not however always sufficient for currently existing technical requirements and are in particular in need of improvement regarding their fastness properties, particularly their thermal stability.

Furthermore, yellow methine dyes having good light fastness are known from EP-A 3 048 138, which also represent an improvement with respect to their thermal stability compared to the prior art presented above, but are nevertheless worthy of further improvement since the performance requirements in terms of polyamide colouration have increased still further.

SUMMARY OF THE INVENTION

The present invention relates to novel methine dyes of the formula (I)

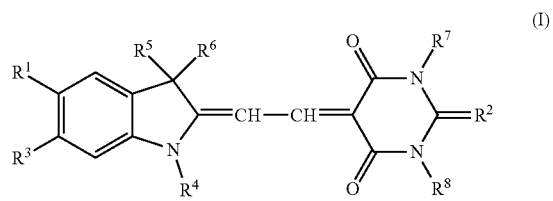

in which
$R^1$ is hydrogen, halogen, alkyl, COOH or $COOR^9$,
$R^2$ is oxygen or sulfur,
$R^3$ is hydrogen, halogen, COOH, $COOR^{10}$ or CN,
$R^4$ is alkyl or phenyl,
$R^5$ and $R^6$ are each independently alkyl,
$R^7$ and $R^8$ are each independently hydrogen, alkyl or $COOR^{11}$, and
$R^9$, $R^{10}$ and $R^{11}$ are each independently alkyl.

DETAILED DESCRIPTION OF THE INVENTION

Alkyl in the definitions of $R^1$ and $R^4$ to $R^{11}$ refers for example to straight-chain or branched $C_1$-$C_6$-alkyl, preferably straight-chain or branched $C_1$-$C_4$-alkyl, especially methyl, ethyl, n- and isopropyl and also n-, iso- and tert-butyl, which may in each case be optionally mono- or polysubstituted by the same or different substituents, for example by halogen, such as chlorine, bromine or fluorine, and also by —OH, —CN, —$NH_2$ or $C_1$-$C_6$-alkoxy.

Halogen in the definitions of $R^1$ and $R^3$ refers for example to fluorine, chlorine or bromine.

In an alternative embodiment, the present invention relates to methine dyes of the formula (I),
in which
$R^1$ is hydrogen, halogen, alkyl, COOH or $COOR^9$,
$R^2$ is oxygen or sulfur,
$R^3$ is hydrogen, halogen, COOH, $COOR^{10}$ or CN,
$R^4$ is alkyl or phenyl,
$R^5$ and $R^6$ are each independently alkyl,
$R^7$ and $R^8$ are each independently hydrogen, alkyl or $COOR^{11}$, and
$R^9$, $R^{10}$ and $R^{11}$ are each independently alkyl,
with the condition that $R^1$ and $R^3$ are not both hydrogen.
Preference is given to dyes of the formula (I),
in which
$R^1$ is hydrogen, halogen, $C_1$-$C_4$-alkyl, which is optionally mono- to trisubstituted, identically or differently, by halogen, COOH or $COOR^9$,
$R^2$ is oxygen or sulfur,
$R^3$ is hydrogen, halogen, $COOR^{10}$ or CN,
$R^4$ is $C_1$-$C_4$-alkyl or phenyl,
$R^5$ and $R^6$ are each independently $C_1$-$C_4$-alkyl,
$R^7$ and $R^8$ are each independently hydrogen, halogen, $C_1$-$C_4$-alkyl, which is optionally mono- to trisubstituted, identically or differently, by methoxy or ethoxy, or $COOR^{11}$, and
$R^9$, $R^{10}$ and $R^{11}$ are each independently $C_1$-$C_4$-alkyl.
In an alternative embodiment, preference is given to dyes of the formula (I),
in which
$R^1$ is hydrogen, halogen, $C_1$-$C_4$-alkyl, which is optionally mono- to trisubstituted, identically or differently, by halogen, COOH or $COOR^9$,
$R^2$ is oxygen or sulfur,
$R^3$ is hydrogen, halogen, $COOR^{10}$ or CN, $R^4$ is $C_1$-$C_4$-alkyl or phenyl, $R^5$ and $R^6$ are each independently $C_1$-$C_4$-alkyl, $R^7$ and $R^8$ are each independently hydrogen, halogen, $C_1$-$C_4$-alkyl, which is optionally mono- to trisubstituted, identically or differently, by methoxy or ethoxy, or $COOR^{11}$, and $R^9$, $R^{10}$ and $R^{11}$ are each independently $C_1$-$C_4$-alkyl, with the condition that $R^1$ and $R^3$ are not both hydrogen.

Particular preference is given to dyes of the formula (I), in which $R^1$ is hydrogen, fluorine, chlorine, $CF_3$ or $COOR^9$, $R^2$ is oxygen or sulfur, $R^3$ is hydrogen, fluorine, chlorine or CN, $R^4$, $R^5$ and $R^6$ are each independently methyl or ethyl, $R^7$ and $R^8$ are each independently hydrogen, each independently unsubstituted methyl, ethyl, n-propyl, isopropyl, n-butyl, isobutyl or tert-butyl; or methyl, ethyl, n-propyl, isopropyl, n-butyl, isobutyl or tert-butyl in each case mono- or disubstituted, identically or differently, by methoxy or ethoxy, and $R^9$ is methyl or ethyl.

In an alternative embodiment, particular preference is given to dyes of the formula (I), in which $R^1$ is hydrogen, fluorine, chlorine, $CF_3$ or $COOR^9$, $R^2$ is oxygen or sulfur, $R^3$ is hydrogen, fluorine, chlorine or CN, $R^4$, $R^5$ and $R^6$ are each independently methyl or ethyl, $R^7$ and $R^8$ are each independently hydrogen, each independently unsubstituted methyl, ethyl, n-propyl, isopropyl, n-butyl, isobutyl or tert-butyl; or methyl, ethyl, n-propyl, isopropyl, n-butyl, isobutyl or tert-butyl in each case mono- or disubstituted, identically or differently, by methoxy or ethoxy, and $R^9$ is methyl or ethyl, with the condition that $R^1$ and $R^3$ are not both hydrogen.

Very particular preference is given to dyes of the formula (I), in which $R^1$ is fluorine, chlorine, $CF_3$ or $COOR^9$, $R^2$ is oxygen or sulfur, $R^3$ is hydrogen, $R^4$, $R^5$ and $R^6$ are each methyl, $R^7$ and $R^8$ are each independently hydrogen, each independently unsubstituted methyl, ethyl, n-propyl, isopropyl, n-butyl, isobutyl or tert-butyl or 1-methyl-2-methoxyethyl, and $R^9$ is methyl.

Dyes of the formula (I) can exist as stereoisomers. Formula (I) particularly includes the following four E and Z isomers of the formulae (Ia) to (Id):

wherein the substituents $R^1$ to $R^8$ have the general and preferred definitions specified for formula (I).

In a further alternative embodiment, the present invention relates to methine dyes of the formula (Ia), in which the substituents $R^1$ to $R^8$ have the general and preferred definitions specified for formula (I).

Using the dyes of the formula (I) according to the invention, yellow to orange colouration of plastics, especially of polyamides, can be achieved, which are characterized by improved light fastness and improved thermal stability compared with the known yellow dyes used for these purposes. Moreover, the dyes according to the invention, surprisingly, also have improved colour strength compared to the known dyes.

It is possible using the dyes according to the invention to significantly outperform the property profiles achieved to date of known yellow dyes for plastic colouration. The present invention further relates to the use of the dyes of the formula (I) according to the invention for the bulk colouration of plastics. The dyes according to the invention can be used here individually or in any desired mixture with one another.

Bulk colouration in this case is understood to mean in particular methods in which the dye is incorporated into the molten plastic material, e.g. with the aid of an extruder, or in which the dye is already added to the starting components for preparing the plastic, e.g. to monomers prior to polymerization.

Particularly preferred plastics are thermoplastics, for example vinyl polymers, polyesters, polyamides and also polyolefins, especially polyethylene and polypropylene, polycarbonates and polyamide. Very particular preference is given to polyamides, especially nylon-6.6 and nylon-6.

In the context of the present invention, the term polyamides is used as a designation for synthetic, industrially usable thermoplastic plastics and thus differentiates this substance class from the chemically related proteins. Almost all significant polyamides are derived from primary amines, since the repeating unit consists of the —CO—NH— functional group. In addition, polyamides of secondary amines (—CO—NR—, R=organic radical) also exist. To prepare the polyamides, in particular aminocarboxylic acids, lactams and/or diamines and dicarboxylic acids serve as monomers.

Nylon-6.6 is usually prepared from hexamethylenediamine (HMD) and adipic acid. It is formed by a polycondensation with elimination of water. Nylon-6 is obtainable by ring-opening polymerization of ε-caprolactam with water as starter.

Suitable vinyl polymers are polystyrene, styrene-acrylonitrile copolymers, styrene-butadiene copolymers, styrene-butadiene-acrylonitrile terpolymers, polymethacrylate and polyvinyl chloride among others.

Suitable polyesters are, for example, polyethylene terephthalates, polycarbonates and cellulose esters.

The plastics to be coloured may be present individually or as mixtures with one another, as plastic materials or melts.

When used for the bulk colouration of plastics, the dyes (I) according to the invention are preferably applied in finely divided form, wherein dispersants may be, but do not have to be, used concomitantly.

When used for the bulk colouration of plastics, the dyes (I) according to the invention can be used for example directly in the process of the plastic preparation after the polymerization is complete. In this case, at least one dye (I) according to the invention is preferably mixed in dry form or ground with the plastic granules and this mixture is plasticized and homogenized for example on mixing rollers or in screws. However, the dyes (I) according to the invention may also be added to the molten liquid material and homogeneously distributed by stirring. The material pre-coloured in this way may then be further processed as usual, e.g. by spinning to give bristles, threads etc. or by extrusion or in injection moulding processes to give mouldings.

Since the dyes (I) are resistant to polymerization catalysts, particularly peroxides, it is also possible to add the dyes (I) according to the invention to the monomeric starting materials for the plastic preparation, e.g. of polymethyl methacrylate (PMMA) and then to polymerize in the presence of polymerization catalysts. For this purpose, the dye is preferably dissolved in the monomeric components or mixed intimately with them.

The dyes of the formula (I) according to the invention for colouring the plastics mentioned, especially polyamide, are used preferably in amounts from 0.0001 to 1% by weight, especially 0.01 to 0.5% by weight, based on the amount of polymer.

By adding pigments insoluble in the polymers, for example titanium dioxide, it is possible to obtain corresponding useful covered colourations.

Titanium dioxide may be used in an amount from 0.01 to 10% by weight, preferably 0.1 to 5% by weight, based on the amount of polymer.

The present invention further relates to a method for the bulk colouration of plastics, wherein at least one dye of the formula (I) is mixed in dry form or is ground with at least one plastic, preferably in the form of granules, and this mixture is plasticized and homogenized, e.g. on mixing rollers or in screws.

However, the dyes (I) according to the invention may also be added to the molten liquid material and homogeneously distributed by stirring. It is likewise possible to add the dyes (I) according to the invention to the monomeric starting components in the plastic preparation and then to polymerize.

The material pre-coloured in this way may then be further processed as usual, e.g. by spinning to give bristles, threads etc. or by extrusion or in injection moulding processes to give mouldings.

By means of the method according to the invention, transparent or covered brilliant yellow colourations with very good heat and light resistance are obtained.

To carry out the method according to the invention, it is also possible to use mixtures of the dyes of the formula (I) according to the invention with other dyes and/or inorganic and/or organic pigments.

The present invention further relates to a method for preparing the dyes of the formula (I) according to the invention.

The dyes of the formula (I) according to the invention may be prepared by reacting at least one aldehyde of the formula (II)

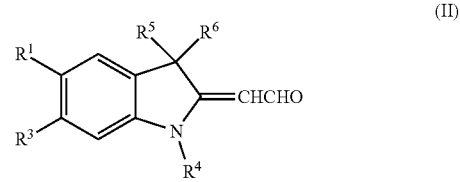

in which
$R^1$, $R^3$, $R^4$, $R^5$ and $R^6$ have the general and preferred definitions specified for formula (I), with at least one barbituric acid derivative of the formula (III)

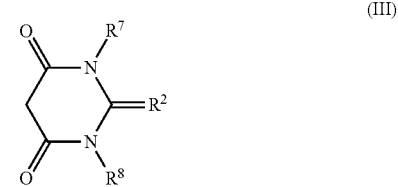

in which
$R^2$, $R^7$ and $R^8$ have the general and preferred definitions specified for formula (I).

The aldehyde of the formula (II) can exist as stereoisomers. The formula (II) includes both possible E and Z forms.

The method for preparing the dyes (I) according to the invention by reacting the aldehydes of the formula (II) with the barbituric acid derivatives of the formula (III) may be carried out in a manner known per se.

The method for preparing the dyes (I) according to the invention is carried out generally at a temperature in the range from −10 to 180° C., preferably from 0 to 100° C. and particularly preferably from 10 to 90° C.

The method for preparing the dyes (I) according to the invention is carried out generally at a pressure from 900 to 1100 hPa, preferably at standard pressure.

The method for preparing the dyes (I) according to the invention can be carried out in the presence of at least one solvent. Suitable solvents are those from the series of alcohols and formamides for example. The method for preparing the dyes (I) according to the invention is preferably carried out in the presence of at least one alcohol from the series of methanol, ethanol, propanol, and/or at least one formamide from the series of dimethylformamide and diethylformamide, particularly preferably in the presence of methanol and/or dimethylformamide.

The method for preparing the dyes (I) according to the invention is carried out in the presence of at least one base. Suitable bases are, for example, alkali metal hydroxides and alkali metal alkoxides. Preference is given to using lithium hydroxide, sodium hydroxide, potassium hydroxide and/or potassium tert-butoxide, particularly preferably sodium hydroxide and/or potassium tert-butoxide.

In general, the method for preparing the dyes (I) according to the invention is carried out such that the aldehyde (II) is firstly initially charged and the barbituric acid derivative (III) is added and, after reaction is complete, the compound of the formula (I) is isolated. The isolation can be carried out by customary processes, preferably by filtration. The reaction product obtained can optionally be worked-up by further method steps such as washing and drying.

To carry out the method, generally 0.8 to 1.5 mol of barbituric acid derivative (III) is used per mole of aldehyde (II). Preferably, 0.9 to 1.1 mol of barbituric acid derivative (III) is used per mole of aldehyde (II) and particularly preferably 1 mol of barbituric acid derivative (III) is used per mole of aldehyde (II).

Barbituric acid derivatives of the formula (III) are known and can be purchased as commercial products from Alfa Acer for example.

The aldehydes of the formula (II) are also known and can be prepared, for example, in a two-stage synthesis in a manner known to those skilled in the art. Here, in a first stage a), at least one indole derivative of the formula (IV)

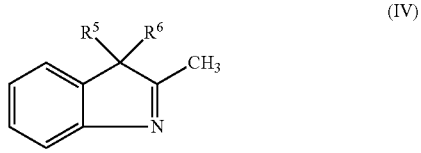

(IV)

in which $R^5$ and $R^6$ have the general and preferred definitions specified for formula (I), is reacted with at least one alkylating reagent and subsequently, in a second stage b), the intermediate of the first stage is reacted with at least one formylation reagent.

Reactions of the kind described in stage b) are known in the literature under the name of Vilsmeier reaction.

Generally, the reaction in stage a) is carried out such that the indole derivative of the general formula (IV) is initially charged and the alkylating agent is added optionally in the presence of a solvent.

The first stage a) of the reaction is carried out generally at a temperature in the range from 10 to 80° C., preferably from 20 to 70° C. and particularly preferably from 30 to 60° C.

The reaction in stage a) is carried out generally at a pressure from 900 to 1100 hPa, preferably at standard pressure.

The reaction in stage a) may be carried out in the presence of at least one solvent. Suitable solvents are those from the series of alcohols and water for example. The reaction in stage a) is preferably carried out in the presence of water as solvent.

In principle, all known alkylating reagents are suitable as alkylating reagent (see e.g. B. K. Schwetlick, Organikum, VEB Deutscher Verlag der Wissenschaften, Berlin, 15th edition 1977, pages 260, 253, 674), such as dimethyl sulfate, methyl iodide or diazomethane. Preference is given to the use of dimethyl sulfate.

In general, at least one mole of alkylating reagent is used per mole of indole derivative. Depending on the structure of the indole derivative, corresponding to the above stoichiometry, even higher molar amounts may be used. Preferably, 0.9 to 1.1 mol, particularly preferably 1 mol of alkylating reagent is used per mole of indole derivative (IV).

The intermediate prepared in stage a) can be isolated by customary methods, by filtration for example. The intermediate prepared in stage a) is preferably further reacted directly without isolation in the subsequent stage b).

In general, the reaction in stage b) is carried out in such a manner that the alkylated compound from the first stage a) in the form of the reaction solution obtained is initially charged and the formylation reagent is added, optionally in the presence of at least one solvent, and subsequently the aldehyde of the formula (II) thus prepared is precipitated, optionally by the addition of a suitable amount of a suitable precipitant, and the aldehyde of the formula (II) is then isolated by customary methods, by filtration for example.

The reaction in stage b) is carried out generally at a temperature in the range from 10 to 80° C., preferably from 20 to 70° C. and particularly preferably from 30 to 60° C.

The reaction in stage b) is carried out generally at a pressure from 900 to 1100 hPa, preferably at standard pressure.

The reaction in stage b) may be carried out in the presence of at least one solvent. Suitable solvents are formamides for example. Preference is given to dimethylformamide and diethylformamide, particular preference being given to the use of dimethylformamide. When using dimethylformamide, it is particularly preferable to use this in excess wherein the dimethylformamide then serves as formylation reagent and solvent at the same time.

The formylation reagent used in stage b) is generally a mixture of at least one formamide and at least one phosphoric acid chloride.

Preferred formamides are dimethylformamide, diethylformamide and dibutylformamide. A preferred phosphoric acid chloride is phosphorus oxychloride.

The formylation reagent used is particularly preferably a mixture of dimethylformamide and phosphorus oxychloride.

In general, at least one mole of formylation reagent, preferably 1.1 to 1.5 mol and particularly preferably 1.1 to 1 mol, is used per mole of alkylated compound from stage 1.

Suitable precipitants are, for example, alcohols such as methanol and/or ethanol.

The precipitant used is preferably methanol and/or ethanol, especially methanol.

The indole derivatives of the formula (IV) are known to those skilled in the art. They may be prepared in a manner known per se in a two-stage synthesis by reacting an aniline derivative of the formula (V)

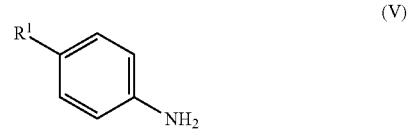

(V)

in which

R¹ has the general and preferred definition specified for formula (I), with a diazotization reagent and subsequent reaction with ring closure with a ketone of the formula (VI)

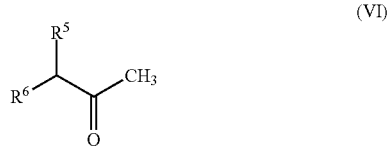
(VI)

in which

R⁵ and R⁶ have the general and preferred definition specified for formula (I).

The diazotization reaction is generally carried out by initially charging the aniline derivative and adding the diazotization reagent at a temperature in the range from 0 to 10° C. at standard pressure in an aqueous medium.

In principle, any suitable diazotization reagent is an option as diazotization reagent. Preference is given to using an aqueous sodium nitrite solution.

In general, the diazotization reagent is used in an amount of at least two moles based on the aniline derivative (V).

The ring closure reaction with the ketone of the formula (VI) is carried out in a manner known per se in a one-pot reaction by reducing the diazonium salt of the aniline derivative (V) to the hydrazone and by reacting the hydrazone with the ketone of the general formula (VI), preferably at a temperature in the range from 40 to 100° C., preferably in aqueous solution, and subsequently by isolating and washing the indole derivative of the formula (IV) by customary methods, preferably filtration.

The aniline derivatives of the formula (V) and the ketones of the formula (VI) are known and can be purchased as commercial products, from Alfa Acer or Sigma-Aldrich for example.

The invention is elucidated but not limited by the following examples, in which the parts are by weight and percentage values are percent by weight (% by weight).

EXAMPLES

Example 1

Preparation of the Inventive Compound of the Formula (I)

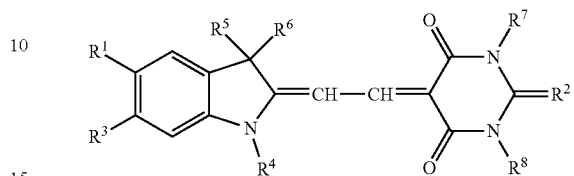

where R¹=COOCH₃; R²=O; R³=H; R⁴, R⁵ and R⁶=CH₃ and R⁷ and R⁸=H

To 160 ml of acetic anhydride were introduced 25.9 g (0.1 mol) of aldehyde of the formula (II) where R¹=COOCH₃; R³=H; R⁴=CH₃ and R⁵ and R⁶=CH₃ and 12.8 g (0.1 mol) of barbituric acid derivative of the formula (III) where R²=O; R⁷ and R⁸=H and 5 g of ammonium chloride. The reaction mixture was subsequently heated to a temperature of 105° C. and stirred for ca. 6 hours. The mixture was then cooled to 25° C., 140 ml of methanol were added and the reaction product isolated on a Nutsche filter. The filter cake was washed with ca. 600 ml of methanol and ca. 2000 ml of water at a temperature of 90° C. The washed product was dried in a vacuum drying cabinet at a temperature of 80° C. and a pressure of 200 h Pa.

Yield: 28.8 g (corresponds to 78% of theory), melting point 361° C.

Examples 2 to 7

Preparation of inventive compounds of the formula (I) in which the substituents R¹ to R⁸ have the definitions listed in Table 1.

TABLE 1

| Example | R¹ | R² | R³ | R⁴ | R⁵ | R⁶ | R⁷ | R⁸ |
|---|---|---|---|---|---|---|---|---|
| 2 | COOCH₃ | O | H | CH₃ | CH₃ | CH₃ | CH₃ | H |
| 3 | COOCH₃ | S | H | CH₃ | CH₃ | CH₃ | C₂H₅ | OCH₃ |
| 4 | CF₃ | O | H | CH₃ | CH₃ | CH₃ | CH₃ | H |
| 5 | Cl | O | H | CH₃ | CH₃ | CH₃ | CH₃ | H |
| 6 | F | O | H | CH₃ | CH₃ | CH₃ | CH₃ | H |
| 7 | COOCH₃ | O | H | CH₃ | CH₃ | CH₃ | —CH—(CH₃)—(CH₂OCH₃) | C₄H₉ |

The preparation and work-up of the compounds of examples 2 to 7 were each carried out in analogy to example 1 but with the following deviations:

Example 2

Instead of the barbituric acid derivative used in example 1, 15.6 g (0.1 mol) of barbituric acid derivative of the formula (III) were used where R²=O; and R⁷ and R⁸=CH₃.

Yield: 33.3 g (corresponds to 84% of theory), melting point 298° C.

Example 3

Instead of the barbituric acid derivative used in example 1, 20.0 g (0.1 mol) of barbituric acid derivative of the formula (III) were used where $R^2=S$; and $R^7$ and $R^8=C_2H_5$.

Yield: 38.4 g (corresponds to 87% of theory), melting point 277° C.

Example 4

Instead of the aldehyde used in example 1, 25.9 g (0.1 mol) of aldehyde of the formula (II) were used where $R^1=CF_3$; $R^3=H$; and $R^4$, $R^5$ and $R^6=CH_3$, and instead of the barbituric acid derivative used in example 1, 15.6 g (0.1 mol) of barbituric acid derivative of the formula (III) were used where $R^2=O$; and $R^7$ and $R^8=CH_3$.

Yield: 33.8 g (corresponds to 86% of theory), melting point 253° C.

Example 5

Instead of the aldehyde used in example 1, 25.9 g (0.1 mol) of aldehyde of the formula (II) were used where $R^1=Cl$; $R^3=H$; and $R^4$, $R^5$ and $R^6=CH_3$, and instead of the barbituric acid derivative used in example 1, 15.6 g (0.1 mol) of barbituric acid derivative of the formula (III) were used where $R^2=O$; and $R^7$ and $R^8=CH_3$ and also 20 g of ammonium chloride.

Yield: 34.4 g (corresponds to 92% of theory), melting point 355° C.

Example 6

Instead of the aldehyde used in example 1, 25.9 g (0.1 mol) of aldehyde of the formula (II) were used where $R^1=F$; $R^3=H$; and $R^4$, $R^5$ and $R^6=CH_3$, and instead of the barbituric acid derivative used in example 1, 15.6 g (0.1 mol) of barbituric acid derivative of the formula (III) were used where $R^2=O$; and $R^7$ and $R^8=CH_3$ and also 20 g of ammonium chloride.

Yield: 26.6 g (corresponds to 74% of theory), melting point 254° C.

Example 7

Instead of the aldehyde used in example 1, 25.9 g (0.1 mol) of aldehyde of the formula (II) were used where $R^1=COOCH_3$; $R^3=H$; and $R^4$, $R^5$ and $R^6=CH_3$ and also 25.6 g (0.1 mol) of barbituric acid derivative of the formula (III) where $R^2=O$, $R^8=C_4H_9$ and $R^7=-CH(CH_3)(CH_2OCH_3)$.

Yield: 36.1 g (corresponds to 77% of theory), melting point 194° C.

Preparation of the Precursors

Example 8

Preparation of an Aldehyde of the Formula (II)

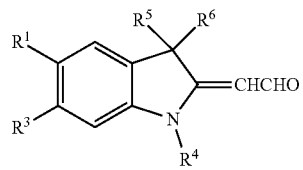

where $R^1=COOCH_3$; $R^3=H$ and $R^4$, $R^5$ and $R^6=CH_3$ a) Diazotization:

139.9 g of p-aminobenzoic acid were introduced to 270 g of 30% hydrochloric acid and the mixture was cooled to 0° C. by externally cooling. Subsequently, 174 g of a 40% aqueous solution of sodium nitrite were added. The mixture was stirred for 30 minutes and then the excess nitrite was removed with ca. 0.5 g of amidosulfonic acid.

b) Preparation of the Hydrazone and Ring Closure:

A mixture of 250 g of water and 660 g of sodium hydrogensulfite, in the form of a 39% aqueous solution, was adjusted to a pH of 6.5 with 80 g of a 40% aqueous sodium hydroxide solution. Over the course of ca. 30 minutes, the diazotization solution prepared in stage a) was added, while maintaining a pH of ca. 6.5 by addition of 100 g of a 40% aqueous sodium hydroxide solution. Subsequently, the reaction mixture was stirred at a temperature of 40° C. for ca. 1 hour. Subsequently, 560 g of 96% sulfuric acid and then 86.1 g of methyl isopropyl ketone were added dropwise. The reaction mixture was heated to 70° C. and stirred for ca. 4 hours. The reaction mixture was subsequently heated to 80° C. and then stirred again for ca. 4 hours. The reaction mixture was then cooled to 25° C. and the pH was adjusted to 6.5 with ca. 800 g of a 40% aqueous sodium hydroxide solution. The reaction mixture was stirred for 30 minutes and the reaction product was then isolated on a Nutsche filter and washed with 2 litres of water.

c) Preparation of the Aldehyde:

The moist press cake of the ring-closed product from stage b) was introduced into 1200 g of water. The pH was then adjusted to 10 with ca. 70 g of a 40% aqueous sodium hydroxide solution. Over the course of 1 hour, 325 g of dimethyl sulfate were added dropwise maintaining a pH here of ca. 8.5 by addition of 200 g of a 40% aqueous sodium hydroxide solution. The reaction mixture was heated to 40° C. and stirred for ca. 5 hours. The reaction mixture was subsequently heated to 60° C. and then stirred for a further 1 hour. The reaction mixture was then left to stand whereupon a phase separation took place within 1 hour. The aqueous phase was then removed. Residual water was removed from the organic phase under reduced pressure at 80° C. and 20 hPa. 310 g of dimethylformamide were then added dropwise to the organic phase. Subsequently, 263 g of phosphorus oxychloride were added at 40° C. over the course of 3 hours and the reaction mixture was stirred for 5 hours. The mixture was then cooled to 20° C. and 160 g of methanol were added. The pH was then adjusted to 11 with ca. 200 g of a 40% aqueous sodium hydroxide solution. The reaction mixture was subsequently stirred for 60 minutes and then the reaction product was isolated on a Nutsche filter and washed with 160 g of methanol and 2000 g of water. The washed product was dried in a vacuum drying cabinet at a temperature of 80° C. and a pressure of 200 h Pa.

Yield: 176.3 g (corresponds to 68% of theory)

Examples 9 to 11

Preparation of aldehydes of the formula (II) in which the substituents $R^1$ and $R^3$ to $R^6$ have the definitions listed in Table 2.

TABLE 2

| Example | $R^1$ | $R^3$ | $R^4$ | $R^5$ | $R^6$ |
|---------|-------|-------|-------|-------|-------|
| 9 | Cl | H | $CH_3$ | $CH_3$ | $CH_3$ |
| 10 | F | H | $CH_3$ | $CH_3$ | $CH_3$ |
| 11 | $CF_3$ | Cl | $CH_3$ | $CH_3$ | $CH_3$ |

Example 9 a) Diazotization:

The preparation of the diazotization was carried out as specified in example 8 a), but 268 g of 30% hydrochloric acid and 127.6 g of 4-chloroaniline were used instead of 270 g of 30% hydrochloric acid and 139.9 g of p-aminobenzoic acid.

b) Preparation of the Hydrazone:

The preparation of the hydrazone and the ring closure were carried out in analogy to example 8 b), but the diazotization solution from step 9 a) was used.

c) Preparation of the Aldehyde:

The moist press cake of the ring-closed product from stage b) was introduced into 1200 g of water. The pH was then adjusted to 10 with ca. 5 g of a 40% aqueous sodium hydroxide solution. Over the course of 1 hour, 153 g of dimethyl sulfate were added dropwise maintaining a pH here of ca. 8.5 by addition of 90 g of a 40% aqueous sodium hydroxide solution. The reaction mixture was heated to 40° C. and stirred for ca. 5 hours. The reaction mixture was subsequently heated to 60° C. and then stirred for a further 1 hour. The reaction mixture was then left to stand whereupon a phase separation took place within 1 hour. The aqueous phase was then removed. Residual water was removed from the organic phase under reduced pressure at 80° C. and 20 hPa. 275 g of dimethylformamide were then added dropwise to the organic phase. Subsequently, 116 g of phosphorus oxychloride were added at 40° C. over the course of 3 hours and the reaction mixture was stirred for 5 hours. The mixture was then cooled to 20° C. and 160 g of methanol were added. The pH was then adjusted to 11 with ca. 180 g of a 40% aqueous sodium hydroxide solution. The reaction mixture was subsequently stirred for 60 minutes and then the reaction product was isolated on a Nutsche filter and washed with 160 g of methanol and 2000 g of water. The washed product was dried in a vacuum drying cabinet at a temperature of 80° C. and a pressure of 200 hPa.

Yield: 141.4 g (corresponds to 60% of theory)

Example 10 a) Diazotization:

The preparation of the diazotization was carried out as specified in example 8 a). However, 375 g of 30% hydrochloric acid and 155.5 g of 3-fluoroaniline were used instead of 270 g of 30% hydrochloric acid and 139.9 g of p-aminobenzoic acid.

b) Preparation of the Hydrazone and Ring Closure:

A mixture of 250 g of water and 918 g of sodium hydrogensulfite, in the form of a 39% aqueous solution, was adjusted to a pH of 6.5 with 120 g of a 40% aqueous sodium hydroxide solution. Over the course of ca. 30 minutes, the diazotization solution prepared in stage a) was added, while maintaining a pH of ca. 6.5 by addition of 140 g of a 40% aqueous sodium hydroxide solution. Subsequently, the reaction mixture was stirred at a temperature of 40° C. for ca. 1 hour. Subsequently, 776 g of 96% sulfuric acid and then 120.4 g of methyl isopropyl ketone were added dropwise. The reaction mixture was heated to 70° C. and stirred for ca. 4 hours. The reaction mixture was subsequently heated to 80° C. and then stirred again for ca. 4 hours. The reaction mixture was then cooled to 25° C. and the pH was adjusted to 6.5 with 1150 g of a 40% aqueous sodium hydroxide solution. The reaction mixture was stirred for 30 minutes and the reaction product was then isolated on a Nutsche filter and washed with 2 litres of water.

c) Preparation of the Aldehyde:

The moist press cake of the ring-closed product from stage b) was introduced into 1200 g of water. The pH was then adjusted to 10 with 10 g of a 40% aqueous sodium hydroxide solution. Over the course of 1 hour, 194 g of dimethyl sulfate were added dropwise maintaining a pH here of ca. 8.5 by addition of 120 g of a 40% aqueous sodium hydroxide solution. The reaction mixture was heated to 40° C. and stirred for ca. 5 hours. The reaction mixture was subsequently heated to 60° C. and then stirred for a further 1 hour. The reaction mixture was then left to stand whereupon a phase separation took place within 1 hour. The aqueous phase was then removed. Residual water was removed from the organic phase under reduced pressure at 80° C. and 20 hPa. 350 g of dimethylformamide were then added dropwise to the organic phase. Subsequently, 147 g of phosphorus oxychloride were added at 40° C. over the course of 3 hours and the reaction mixture was stirred for 5 hours. The mixture was then cooled to 20° C. and 160 g of methanol were added. The pH was then adjusted to 11 with ca. 200 g of a 40% aqueous sodium hydroxide solution. The reaction mixture was subsequently stirred for 60 minutes and then the reaction product was isolated on a Nutsche filter and washed with 160 g of methanol and 2000 g of water. The washed product was dried in a vacuum drying cabinet at a temperature of 80° C. and a pressure of 200 h Pa.

Yield: 169.1 g (corresponds to 55% of theory)

Example 11 a) Diazotization:

161.1 g of 4-trifluoromethylaniline were added dropwise to 375 g of 30% hydrochloric acid and the mixture was then cooled by external cooling to 0° C. Subsequently, 244 g of a 40% aqueous solution of sodium nitrite were added. The reaction mixture was stirred for 30 minutes and then the excess nitrite was removed by adding ca. 0.5 g of amidosulfonic acid.

b) Preparation of the Hydrazone and Ring Closure:

In a mixture of 250 g of water and 918 g of 39% sodium hydrogen sulfite solution, the pH was adjusted to ca. 6.5 by the addition of ca. 120 g of a 40% aqueous sodium hydroxide solution. Over the course of 30 minutes, the diazotization solution from stage a) was added while maintaining a pH of 6.5 by addition of ca. 140 g of a 40% aqueous sodium hydroxide solution. Subsequently, the reaction mixture was stirred at a temperature of 40° C. for ca. 1 hour. Subsequently, 776 g of 96% sulfuric acid and then 120.4 g of methyl isopropyl ketone were added dropwise. The reaction mixture was heated to 70° C. and then stirred for ca. 4 hours. The reaction mixture was subsequently heated to 80° C. and then stirred again for ca. 4 hours. The mixture was then cooled to 25° C. and the pH was adjusted to ca. 6.5 with ca. 1150 g of a 40% aqueous sodium hydroxide solution. The reaction mixture was stirred for 30 minutes and the reaction product was then isolated on a Nutsche filter and washed with 2 litres of water.

c) Preparation of the Aldehyde:

The moist press cake of the ring-closed product from stage b) was introduced into 1200 g of water. The pH was then adjusted to ca. 10 with ca. 10 g of a 40% aqueous sodium hydroxide solution. Over the course of ca. 1 hour, 194 g of dimethyl sulfate were added dropwise maintaining a pH here of ca. 8.5 by addition of ca. 120 g of a 40% aqueous sodium hydroxide solution. The reaction mixture was heated to 40° C. and stirred for 5 hours. The mixture was subsequently heated to 60° C. and stirred for 1 hour. The reaction mixture was allowed to stand for ca. 1 hour until phase separation had occurred. The aqueous phase was then removed. Residual water was removed from the organic phase at 80° C. and 20 hPa. 350 g of dimethylformamide were then added dropwise to the organic phase. Subsequently, 147 g of phosphorus oxychloride were added at 40° C. over the course of 3 hours. The reaction mixture was further stirred for 5 hours, then cooled to 20° C. and 160 g of methanol were added. The pH was then adjusted to ca. 11 by addition of ca. 200 g of a 40% aqueous sodium hydroxide solution. The mixture was stirred for 60 minutes and the reaction product was then isolated on a Nutsche filter and washed with 160 g of methanol and 2000 g of water. The washed product was dried in a vacuum drying cabinet at a temperature of 80° C. and a pressure of 200 hPa.

Yield: 137.3 g (corresponds to 51% of theory)

Example 12

Preparation of a Barbituric Acid Derivative of the Formula (III)

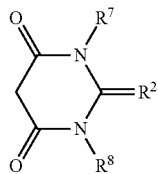

where $R^2$=O; $R^8$=$C_4H_9$ and $R^7$=—CH($CH_3$)($CH_2OCH_3$)

89.1 g (1.0 mol) of 2-amino-1-methoxypropane were introduced into 500 ml of toluene. The reaction mixture was then heated to 50° C. Over the course of ca. 2 hours, 99.1 g (1.0 mol) of butyl isocyanate were added dropwise and the mixture was then stirred for ca. 2 hours. The solvent was distilled off at 80° C. and 20 hPa and then 220 g of acetic acid and 104.1 g (1.0 mol) of malonic acid were added. The reaction mixture was heated to 65° C. and 391 g of acetic anhydride were added dropwise over the course of ca. 3 hours. The mixture was further stirred for one hour and the solvent was then distilled off at 80° C. and 20 hPa. To the residue were added 700 ml of cyclohexane, which was brought to boiling point, and 2 g of Tonsil-fuller's earth (manufacturer: Clariant) were added. The reaction mixture was then cooled to 25° C. and filtered through a laboratory Nutsche filter. The filtrate was then concentrated at 50° C. and 20 hPa.

Yield: 245 g of a solution in cyclohexane having a product content of 60% by weight (content determination by NMR); corresponding to a yield of 57% of theory.

| List of substances purchased | | | | |
|---|---|---|---|---|
| Name: | Molecular weight | Cas. No. | Content | Manufacturer |
| p-Aminobenzoic acid | 137.2 | 150-13-0 | 98 | Sigma-Aldrich |
| Methyl isopropyl ketone Isopropyl methyl ketone | 86.1 | 563-80-4 | 99 | Sigma-Aldrich |
| 4-Chloroaniline | 127.6 | 106-47-8 | 98 | Sigma-Aldrich |
| 4-Fluoroaniline | 111.1 | 371-40-4 | 99 | Alfa Acer |

| List of substances purchased | | | | |
|---|---|---|---|---|
| Name: | Molecular weight | Cas. No. | Content | Manufacturer |
| 4-Trifluoromethylaniline | 161.1 | 455-14-1 | 99 | Sigma-Aldrich |
| Barbituric acid | 128.1 | 67-52-7 | 99 | Sigma-Aldrich |
| 1,3-Dimethylbarbituric acid | 156.1 | 769-42-6 | 99 | Merck |
| 1,3-Diethyl-2-thiobarbituric acid | 200.3 | 5217-47-0 | 99 | Alfa Acer |
| 2-Amino-1-methoxypropane | 105.1 | 37143-54-7 | 99 | Sigma-Aldrich |
| Butyl isocyanate | 99.1 | 11-36-4 | 98 | Sigma-Aldrich |

The results of the UV/VIS measurements and absorption values for the inventive compounds of Examples 1 to 7 are listed in Table 3.

TABLE 3

| Inventive compound | Absorption maximum UV/VIS spectrum[1] | E 1/1 value[2] |
|---|---|---|
| Example 1 | 463 nm | 2634 |
| Example 2 | 466 nm | 2562 |
| Example 3 | 493 nm | 3226 |
| Example 4 | 458 nm | 2290 |
| Example 5 | 464 nm | 2418 |
| Example 6 | 458 nm | 2244 |
| Example 7 | 467 nm | 2131 |

[1]The UV/VIS absorption spectra of the inventive compounds were all measured in the solvent 1-methoxy-2-propyl acetate (CAS No. 108-65-6).
[2]The E 1/1 value specified is a hypothetical absorption value. Initially measured is the absorbance of a solution of the respective sample in 1-methoxy-2-propyl acetate in a cuvette of 1 cm path length, wherein the concentration of the solution is selected such that the absorption value observed at the absorption maximum is about 1. The value determined is then converted to a concentration of 1 percent by weight whereby the E 1/1 value is obtained.

Practical Results:

A) Description of the "Thermal Stability" Test Method

In a tumbling mixer, 2 g each of the dye to be tested were mixed with 1998 g of a PA6 granulate of the Durethan B3OS type (commercial product from Lanxess Deutschland GmbH) with 1% $TiO_2$ which had been dried at 80° C. for 4 hours. This mixture was extruded at a material temperature of at most 240° C. in a single-screw extruder (Stork, 25 mm screw), cooled with water, granulated using a granulator from Sheer and dried at 80° C. for 8 hours. The heat stability of the resulting plastic granules was tested according to DIN EN 12877-2 ("Determination of colour stability to heat during processing of colouring materials in plastics") (method A) on an injection moulding machine. A sample as standard was prepared at 240° C. with a residence time in the screw of 2.5 minutes. Compared to this standard sample, the samples to be determined were evaluated coloristically, which were prepared at a residence time of 5 minutes and temperatures of 240-320° C. Samples with an overall colour difference (calculated in accordance with EN ISO 11664-4) of dE 3.0 were evaluated as stable at the applied temperature.

The results of the thermal stability determination of the inventive compounds of Examples 1 to 7 and also the non-inventive comparative compounds of the prior art are listed in Tables 5 and 6.

TABLE 4

| Inventive compound | Heat stable to (° C.) |
|---|---|
| Example 1 | 340 |
| Example 2 | 335 |
| Example 3 | 345 |
| Example 4 | 335 |
| Example 5 | 340 |
| Example 6 | 340 |
| Example 7 | 335 |

TABLE 5

| Non-inventive compound | Heat stable to (° C.) |
|---|---|
| D. Y 201 (Macrolex Yellow 6G) | Decolorization at 240° C. |
| S. Y. 93 (Macrolex Yellow 3G) | Decolorization at 240° C. |
| S. Y 114 (Macrolex Yellow G) | 240° C. |
| S. Y 160:1 (Macrolex Fluor. Yellow 10GN) | <240° C. (DE 3.6 at 240° C.) |
| Example 8 of EP-A 3 048 138 | 320° C. |
| Example 9 of EP-A 3 048 138 | 320° C. |

What is claimed is:

1. A dye of the formula (I)

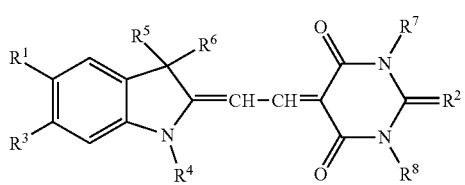

(I)

in which
R$^1$ is hydrogen, halogen, C$_1$-C$_4$-alkyl, which is optionally mono- to trisubstituted, identically or differently, by halogen, COOH or COOR$^9$,
R$^2$ is oxygen,
R$^3$ is hydrogen, halogen, COOR$^{10}$ or CN,
R$^4$ is C$_1$-C$_4$-alkyl or phenyl,
R$^5$ and R$^6$ are each independently C$_1$-C$_4$-alkyl,
R$^7$ and R$^8$ are each independently hydrogen, halogen, C$_1$-C$_4$-alkyl, which is optionally mono- to trisubstituted, identically or differently, by methoxy or ethoxy, or COOR$^{11}$, and
R$^9$, R$^{10}$ and R$^{11}$ are each independently C$_1$-C$_4$-alkyl, and
where R$^1$ and R$^3$ are not both hydrogen.

2. The dye of claim 1, wherein in formula (I)
R$^1$ is hydrogen, fluorine, chlorine, CF$_3$ or COOR$^9$,
R$^2$ is oxygen,
R$^3$ is hydrogen, fluorine, chlorine or CN,
R$^4$, R$^5$ and R$^6$ are each independently methyl or ethyl,
R$^7$ and R$^8$ are each independently hydrogen, each independently unsubstituted methyl, ethyl, n-propyl, isopropyl, n-butyl, isobutyl or tert-butyl; or methyl, ethyl, n-propyl, isopropyl, n-butyl, isobutyl or tert-butyl in each case mono- or disubstituted, identically or differently, by methoxy or ethoxy, and
R$^9$ is methyl or ethyl.

3. The dye of claim 1, wherein in formula (I)
R$^1$ is fluorine, chlorine, CF$_3$ or COOR$^9$,
R$^2$ is oxygen,
R$^3$ is hydrogen,
R$^4$, R$^5$ and R$^6$ are each methyl,
R$^7$ and R$^8$ are each independently hydrogen, each independently unsubstituted methyl, ethyl, n-propyl, isopropyl, n-butyl, isobutyl or tert-butyl or 1-methyl-2-methoxyethyl, and
R$^9$ is methyl.

4. A method for producing a dye of claim 1, the method comprising contacting an aldehyde of the formula (II)

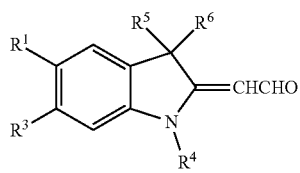

(II)

in which R$^1$, R$^3$, R$^4$, R$^5$, R$^6$, have the definitions specified in claim 1,
with a barbituric acid derivative of the formula (III)

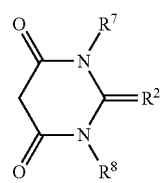

(III)

in which R$^2$, R$^7$, and R$^8$ have the definitions specified in claim 1.

* * * * *